United States Patent [19]

Presser

[11] Patent Number: 4,499,377

[45] Date of Patent: Feb. 12, 1985

[54] DETECTION AND CONTROL SYSTEM BASED ON AMBIENT AIR QUALITY

[75] Inventor: Gustave S. Presser, Quebec, Canada

[73] Assignee: Acme Engineering Products Ltd., Montreal, Canada

[21] Appl. No.: 426,980

[22] Filed: Sep. 29, 1982

[51] Int. Cl.$^3$ .............................................. G01N 21/00
[52] U.S. Cl. ................................... 250/343; 250/430; 356/437
[58] Field of Search ..................... 340/632; 356/437; 250/343, 344, 345, 346, 430

[56] References Cited

U.S. PATENT DOCUMENTS

| | | | |
|---|---|---|---|
| 2,768,370 | 10/1956 | Maninger | 340/632 |
| 2,908,820 | 10/1959 | Parsons | 250/346 |
| 3,562,522 | 2/1971 | Cederstrand et al. | 250/343 |
| 3,678,487 | 7/1972 | Ludewig et al. | 340/632 |
| 3,735,382 | 5/1973 | Soult | 340/632 |
| 3,788,124 | 1/1974 | Teton | 340/632 |
| 4,013,260 | 3/1977 | McClatchie et al. | 250/343 |
| 4,103,174 | 7/1978 | McClatchie et al. | 250/493 |
| 4,177,381 | 12/1979 | McClatchie et al. | 250/343 |
| 4,200,791 | 4/1980 | Burough | 250/343 |
| 4,266,131 | 5/1981 | Ahjopalo et al. | 250/345 |
| 4,340,885 | 7/1982 | Chavis et al. | 340/632 |
| 4,384,925 | 5/1983 | Stetter et al. | 340/632 |

*Primary Examiner*—Alfred E. Smith
*Assistant Examiner*—Carolyn E. Fields

*Attorney, Agent, or Firm*—Larson and Taylor

[57] ABSTRACT

A detection and control system based on ambient air quality is disclosed. The system sequentially monitors the ambient air quality in different locations of a building or the like, and controls other gases such as carbon dioxide present in a building. The system has at least one sampling head, with a pump associated with that head, a calibration pump, and a selector for selecting operation time of each pump in sequence, and time lapse between sequences. An analyzer analyzes samples of gas from each sampling head and the calibration pump, the analyzer produces an analysis signal representing quantity of contaminant gas present in each sample. Provision is made for setting a plurality of first predetermined set points representing levels of the contaminant gas which may occur in each sample, a plurality of on/off signals representing when the contaminant gas reaches the first set points are produced. There is also provided a second predetermined set point setting representing a level of the contaminant gas which may occur in each sample and a predetermined proportional range from the second set point for each sample, and an analog signal producer indicating a deviation from the second set point in the proportional range for each sample representing the contaminant gas in each sample, the analog signal for each sample being in a plurality of output ranges of different magnitudes.

9 Claims, 4 Drawing Figures

DETECTION AND CONTROL SYSTEM BASED ON AMBIENT AIR QUALITY

The present invention relates to a device for detecting and controlling ambient air quality in an environment. More particularly, the invention relates an an analyser having a series of sampling heads which can be positioned in different locations and sequentially monitor the conditions in the atmosphere of each location and produce a series of signals representing the air condition. Such conditions include the quantity of carbon dioxide or carbon monoxide present in the air, humidity and temperature of the atmosphere.

In order to save energy in non-residential buildings, a trend has started to recirculate internal air and minimize the quantity of outside air brought into a building. Such a system utilizes the heat within the building and reduces the heating or the cooling of the outside air brought into the building. In this way, heating and cooling costs are kept to a minimum. In order to utilize this recirculation of air within a building, it is essential to ensure that the quality of air in the building is preserved, and one method of controlling the air quality is by measuring the carbon dioxide present in the air. In the past, carbon dioxide sensors have been expensive and difficult to operate. On the whole, they are accurate provided you have an expert operator who can calibrate the equipment every day. Other methods of ensuring air quality are detecting and controlling other gases present in the air, and controlling temperature and humidity.

It is the purpose of the present invention to provide an analyser which has a number of sampling heads for different locations within a building and which can analyse the conditions in the atmosphere present in each of the sampling locations and then produce a signal for each location which is linked to the ventilation system of the building to open dampers, operate fans, or to operate heaters, scrubbers, humidifiers or dehumidifiers, and ensure that the required quality of air is maintained within all locations in a building. The analyser may also be attached to a recording system to record the air quality, and to an alarm to signal a dangerous condition. Another feature of the analyser is to provide an indication of the contaminant levels at each sampling point by looking at a simple sequence display. It is a further purpose to provide an analyser which is simple to operate and maintain, versatile and compatible with practically all existing building control systems whether electric, electronic or pneumatic.

An analyser which measures the carbon dioxide present in an environment in different locations of a building may be used in a variety of installations. Schools and universities, for instance, could have sampling heads positioned in a gym, auditorium, lecture rooms and the like. Thus, the ventilation of these areas would be increased when they were in use, but would be closed down when they were not in use because the requirement for fresh air would be reduced. Other examples of using such an analyser are, department stores, food stores, theatres, cinemas, assembly halls, arenas, office buildings.

Other uses of a detection and control system for ambient air include control of carbon dioxide level in greenhouses, and storage plants for fruits and vegetables. Personnel protection may be provided with a carbon dioxide analyser in breweries, bottling plants, wineries, quick freezing establishments, dry-ice plants, bakeries, etc.

The present invention provides an ambient air quality detection and control system for at least one sampling position, comprising at least one sampling head, each head for location in a sampling position, at least one pump, one pump for each sampling head, for pumping a sample of gas from each sampling head, a calibration pump having a filter means to provide clean gas, a selector means for selecting operation time of each pump individually and time lapse between sequences, an analyser for analysing samples of gas from each sampling head and the calibration pump, the analyser producing an analysis signal representing quantity of contaminant gas present in each sample, means for setting a plurality of first predetermined set points representing levels of the contaminant gas which may occur in each sample, means for producing a plurality of on/off signals representing when the contaminant gas in each sample reaches the first set points, means for setting a second predetermined set point representing a level of the contaminant gas which may occur in each sample and a predetermined proportional range from the second set point for each sample, and means for producing an analog signal indicating a deviation from the second set point in the proportional range for each sample representing the contaminant gas in each sample, the analog signal for each sample being in a plurality of output ranges of different magnitudes.

In further embodiments the system of the present invention includes the value of the analysis signal from each sample indicated on a seven segment display in a sequence identifying the particular sampling head with the value for that sample, the sequence being on a preset time basis independent of which of the plurality of pumps is in operation. A calibration means may also be provided to operate with the calibration pump to produce a new zero base value and adjust the analysis signal accordingly, after a series of sequences and before commencing a further series of sequences.

In another embodiment a timing means is associated with the selector means to set a predetermined time for the individual operation of each pump dependent upon the distance between the sampling head and the appropriate pump. A means for setting a time period for the commencement of a complete sequence to operate all the pumps in a desired order may also be provided.

In yet another embodiment, a display means is provided which indicates which pump is in operation. Furthermore, one of the output ranges of the analog signal for each sample is a pneumatic signal.

In a further embodiment the analyser analyses the quantity of carbon dioxide gas present in the sample gas. The analyser may be an infrared analyser with a rotating chopper having a filter therein and the analysis signal represents the level of carbon dioxide gas present in each sample acquired at specific selected times synchronized with pump operating time representing distance from the sampling point to the analyser.

In drawings which illustrate the embodiments of the invention,

FIG. 3 illustrates a typical terminal strip for one sampling point.

Figure 1:
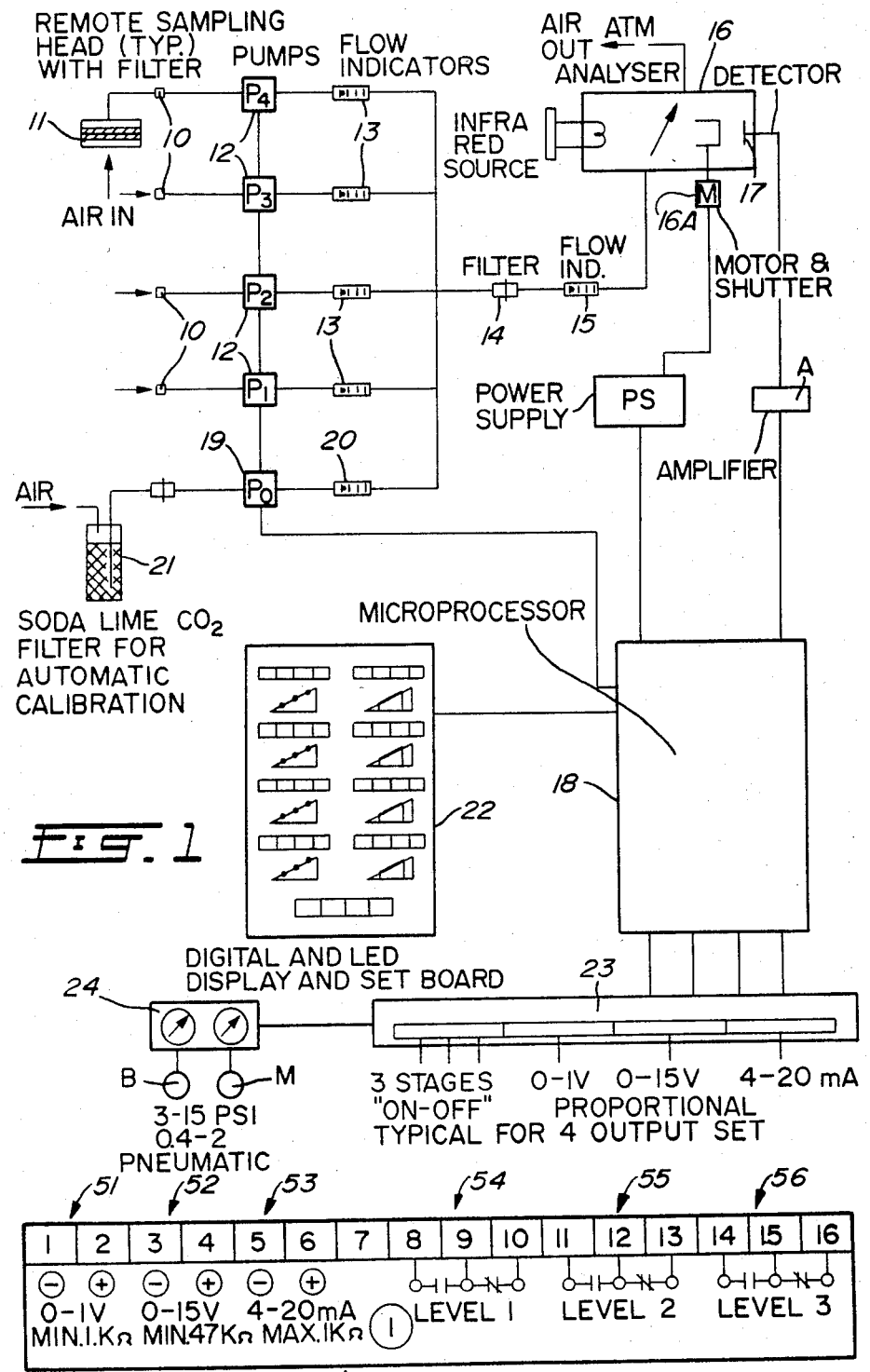
FIG. 1 is a schematic diagram showing one example of an ambient air quality detection and control system of the present invention.

In the schematic diagram of FIG. 1 four sampling points 10 are shown with the top sampling point having a filter 11. Filters are preferably used at each sampling point. Each of these sampling points 10 is located in a different location. In the case of a building, they are in different rooms and have a tube or pipe connection to the analyser unit itself. The analyser unit comprises four pumps 12, one for each sampling point 10, followed by a flow indicator 13 on each line. The flow lines combine after the flow indicators 13 and a sampling line passes through a filter 14 and a further flow indicator 15 into a cell of an analyser 16. As indicated in FIG. 1, the flow line system has no selector valves.

The example shown is an infrared analyser 16 of a type well known in the art to measure carbon dioxide values. The infrared source emits radiation which is absorbed in proportion to the carbon dioxide concentration in the cell. A motorized rotating shutter 16A has a filter and aperture therein to provide an interrupted beam at a certain frequency which is absorbed by the carbon dioxide gas present in the sample. A detector 17 at the end of the cell measures the beam intensity and produces an output signal proportional to the carbon dioxide concentration. The output signal from the detector 17 is amplified and sent to a microprocessor unit 18 which may also control the operation of the analyser. Although each time the shutter 16A rotates, a signal representing the intensity of the beam passing through the aperture and falling on the detector 17, is fed to the microprocessor unit 18, there is only one measurement acquired representing the analysis of the sample in the analyser 16. This analysis measurement is acquired at the specified time called for by the microprocessor after the sequence time which is set to ensure the gas comes from the sampling point 10, and has flushed out the previous sample and the gas in the sampling tube. The microprocessor unit 18 includes any one of a number of conventional microprocessor chips (e.g. 8080, 8085, 280, 6800 and 9900) RAM's, E-PROM's and conventional interfacing circuitry and peripheral equipment. A computer program and analyzer output characteristics for various ranges are stored in the E-PROM's to operate the system to produce the sequence steps for each sampling point, and the output signals for each analysis. The particular computer program depends upon the particular type of microprocessor chip that is used, and it is easily within the skill of a computer programmer to write a program using the aforedescribed disclosure. Microprocessor unit 18 also includes a clock to provide time information or uses the computer program to keep track of elapsed time to determine the operational sequence. If an additional external clock is used, the computer program receives the information through an interrupt. The other information needed by microprocessor unit 18 may be obtained by polling the analyser after a time delay according to the setting, following the operation of a particular pump 12. The computer program may also convert the information received from analyser 16 to an appropriate form for display by the LED display and seven segment digital display on setting board 22. Conventional analog-to-digital converters are used to provide the information to microprocessor unit 18 in the appropriate digital form. Similarly, digital-to-analog converters may be used to convert the output control signals from microprocessor unit 18 to analog electrical outputs which may then be used to operate pneumatic transducer 24. Finally, the predetermined alarm set points are set by one of the corresponding switches 32 and 33.

A calibration pump 19 has a line passing through a calibration flow meter 20 and connects into the sampling line to the analyser 16 before filter 14. Ambient air is drawn into the calibration pump 19 through a carbon dioxide absorbent filter 21 such as a soda lime filter to ensure that when the air enters the analyser 16 from the calibration pump 19, it is completely free from carbon dioxide and produces a signal for the microprocessor unit 18 to act as a revised zero for comparison with each sampling analysis for the next series of samples until the next calibration. In one embodiment the calibration sample occurs once an hour. A digital display and setting board 22 provides controls for setting parameters for all four sampling positions, and feeds this information to the microprocessor unit 18. It also displays the acquired analysis value of each sampling position sequentially by seven segment digital display devices. The analysis information in digital form from all channels is displayed on a five second cycle basis, representing the figures of the last analysis for each channel regardless of which sampling point is being analysed. A terminal strip 23 as shown in FIG. 1 is provided for each output channel, and a pneumatic transducer 24 is shown to provide a proportional pneumatic signal when the control system of dampers, motors and the like is operated by pneumatic means.

The microprocessor unit 18 provides a cycle wherein each pump 12 operates in a predetermined sequence, including the calibration pump 19, and sufficient time is provided for the old air in the system to be removed and new air to flush out the tubing and analyser 16 before an analysis of gas present in the cell is taken. The cycle time may be selected to suit particular requirements. In the case of carbon dioxide, it is generally found that the levels do not fluctuate at a high rate, but have a slow build up. Thus, a cycle that can be adjusted from continuous to every 90 minutes is generally acceptable for control of almost any environment within a building.

Figure 2:
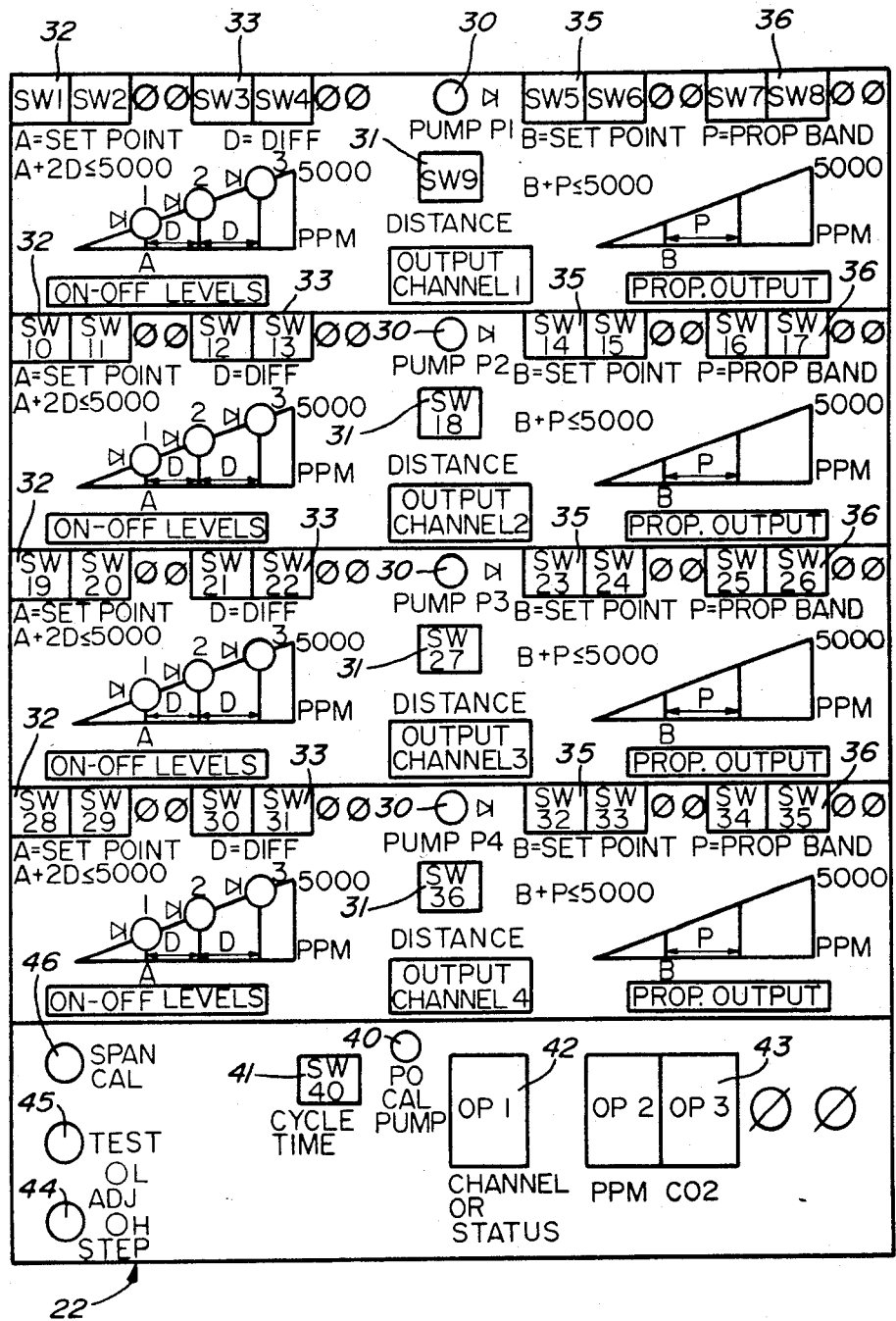
FIG. 2 is a view of a display and setting board for the system of the present invention.

A typical setting board 22, with digital displays is shown in FIG. 2. The first four sections of the panel represent the set and display for each of the four pumps, sampling positions and output channels. The lower section has the seven segment digital display of contaminant gas analysis and channel indication together with a selection of the time cycle. Indicator lights 30 on each of the first four sections indicate which pump 12 is in operation. Beneath the indicator light 30 there is a distance switch 31 which sets the time so that when a pump is switched on, air flows from the sampling position 10 through the pump 12 and all the piping associated with it, and then through the analyser 16 to flush out any existing air in the piping and analyser before the actual analysis occurs. On the left side of each section is an LED indication of three levels of contaminant gas selected for each sample. As illustrated, the range of measurement shown on each section is from 0–5000 parts per million (ppm). Other ranges may be selected dependent upon the type and range of gas contaminant to be analysed. If, for example, an ambient gas condition present in a sample was 400 ppm, then analysis below this figure may be inaccurate. The left hand switches 32 represent the set point which sets the first level somewhere in the desired range, i.e. between 0–5000 ppm. The second series of switches 33 sets the differential distance between the first and second set point, and the second and third set point. This differential difference is the same between the first and second and third levels. For example, if the set point is initially set at 1000 ppm and the differential is set at 1500 ppm, then first level would be 1000, second level would be 2500 and third level would be 4000 ppm. The on/off signals produced when these levels are reached may start a fan motor, open a damper or increase the capacity of a fan driven by a two speed motor. The third level may be used to sound an alarm depending on the particular requirement of the building.

On the right hand side of each section is a diagram showing a set point and a proportional range from 0–5000 ppm. Switches 35 are provided for setting the set point. The set point set at the commencement of the proportional range is not connected with the three set points set by switches 32 and 33. Switches 36 are provided for setting a proportional range. The set point may be positioned anywhere within the range from 0–5000 ppm and a proportional band may be set to be a small portion of that range, namely 100 ppm or it may be set for the full 5000 ppm. The resultant output from the system produces an analog signal representing the contaminant gas analysis in this particular band selected by the set point switches 35 and proportional switches 36.

The lower portion of the panel provides an indicator light 40 to show when the calibration pump 19 is in operation, and a switch 41 to determine the cycle time. In effect, it is found that a thirty minute cycle time for certain applications is satisfactory. The cycle time commences with each pump operating in sequence. The calibration cycle occurs every hour, at start up of operation, or after a shut down such as at night or at the weekends when there is command from a time switch or after a power interruption. The values of the analysis of each sampling position is indicated in the channel digital display 42 with the quantity of contaminant gas shown in the second digital display 43. The digital displays are, in one embodiment, seven segment digital displays capable of showing letters and numerals.

In normal operation the acquired analysis information is displayed in digital form on a five second cycle basis sequentially from sampling point to sampling point regardless of which sampling point is under analysis.

A step button 44 for manual sequencing through the cycle is provided together with a test button 45 to enable the machine to be tested by running through all the sequences in short order. A span calibrate push button 46 is also provided for checking the span calibration when desired. In one example of a 5000 ppm span, the gas analyser produces a signal of 0–5 v. If the required range is set for 2.5 v, then you have a float of 1.25 v above and below the range to take into account the movable zero. It also allows calibration for altitude and barometric pressure variations.

The terminal strip 23, shown for channel 1, and typical for all channels, comprises a number of contacts for connection to fans, dampers, recorders and the like within the building. On the left hand side contacts 51, 52 and 53 provide the proportional outputs for the range set from switches 35 and 36. Terminals 51 show a range from 0–1 volt, terminal 52 shows a range from 0–15 volts and terminal 53 shows a range of from 4–20 milliamps. These three ranges are commonly used in electronic control systems or electronic-electric control systems in the ambient air control field. Similarly, as shown in FIG. 1, the set point and proportional band can be used through an internal transducer to produce a pneumatic signal in the range of 3–15 lbs/sq. inch for a standard pneumatic control system. The 0–1 volt output would normally be used in a recorder which can be provided. Levels 1, 2 and 3 set from switches 32 and 33 have sets of contacts 54, 55 and 56 for connection to fans, motors, dampers alarms and the like. The third level, contacts 56, is generally connected to some form of an alarm system when the contaminant gas content reaches a high level.

Figure 4:
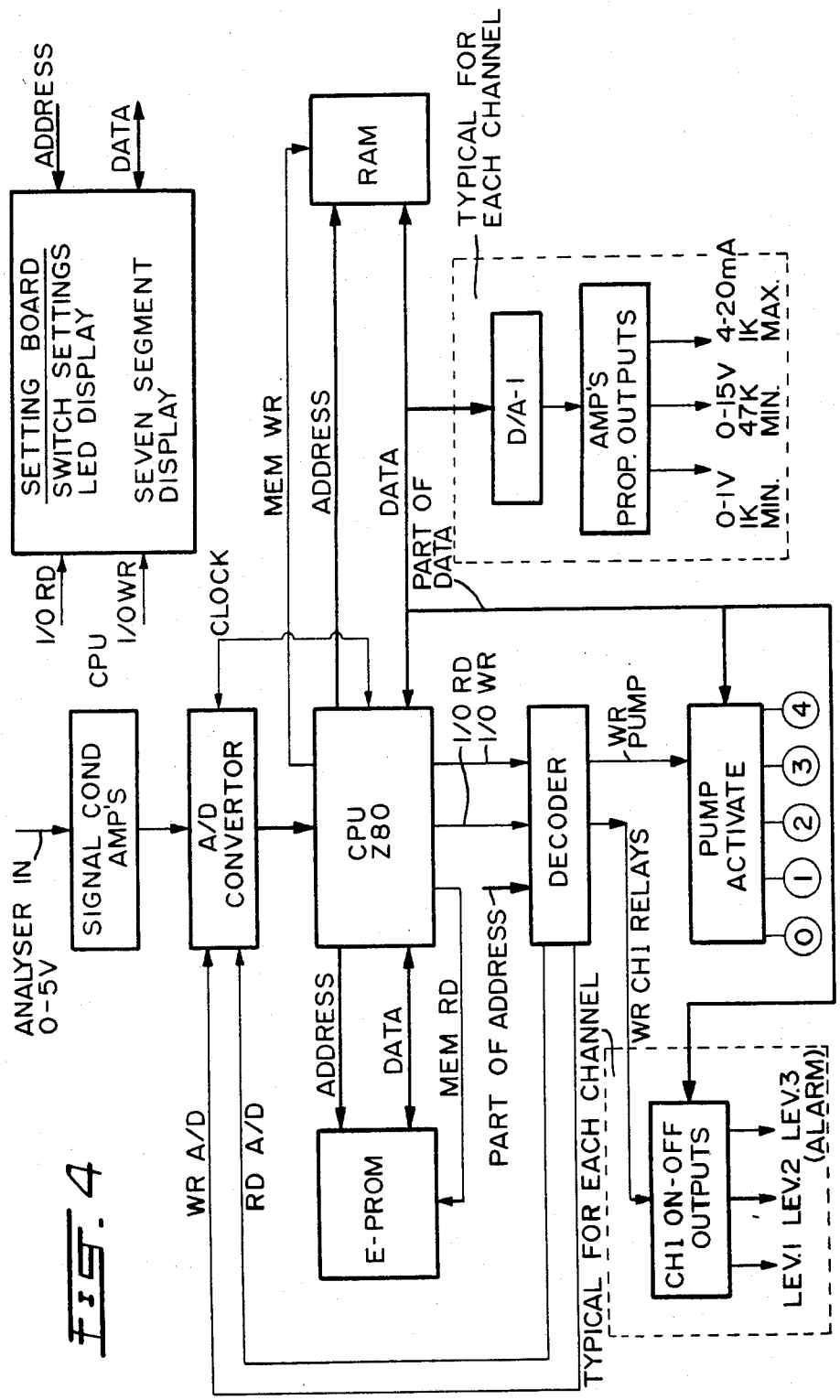
FIG. 4 shows a block diagram of the electronics suitable for the system of the present invention.

An electronic block diagram is shown in FIG. 4 which is suitable for the present invention. The diagram illustrates the electronic function of the microprocessor 18 of FIG. 1.

A zero calibration is included in the system which reprograms the zero setting after each calibration so that the digital display 43 always shows a contaminant gas figure from the last calibrated zero setting.

In one typical operation the following steps occur:

1. Power "on", "heat up" cycle. Immediately after the power is switched on, the unit enters its heat up cycle. The digital display 43 indicates "HU". During this cycle all ON-OFF and proportional outputs are in their low (de-energized) states, all pumps are switched off and only the step button 44 is monitored, for manual override if desired. The unit idles for 30 minutes to allow the analyser to attain its working temperature. At the end of the 30 minutes, the unit enters the sampling cycle.

2. Automatic calibration and sampling cycle. Following the heat up cycle, the unit reverts to normal operation by first taking a calibration sample, then entering the normal sampling cycle.

3. Zero calibration. During this hourly cycle, the digital displays 42 and 43 display C AL. The calibration pump 19 is activated and a contaminant free air sample obtained through the filter 21 is fed to the analyser 16 in order to check and/or adjust the previous zero gas value reading of the unit. The process lasts two minutes and the unit then enters the sampling cycle.

4. Sampling cycle. In this cycle, the amount of contaminant gas in the atmosphere at any of the four sampling positions 10 is determined by reading the analyser output after the atmosphere from the sampling position has been pumped for sufficient time to fully flush the tubing and analyser and to allow the analyser reading to settle. This is done by turning on the required pump 12 for 1½ minutes for each 25 feet of tubing length (based on ¼ inch OD tubing) plus a final 2 minutes.

When all channels have been sampled, the unit either immediately restarts sampling the first channel, or waits for a time determined by the cycle time switch 41. If the time taken to sample all the channels is equal to or greater than the time specified by the cycle time switch 41, sampling immediately starts at the first channel again. This also occurs if the cycle time switch 41 is set to 0, the setting for continuous sampling. If the total sampling times taken is less than the time specified by the cycle time switch 41, the unit waits for the time difference to pass before starting the cycle time again. Every hour during the sampling cycle a calibration sample is run, interrupting the sampling cycle.

Approximately every four minutes during the sampling cycle a self test cycle is carried out by the microprocessor unit 18. The decimal point of the first digit of the 7-segment display 42 is lit during the test to indicate this. In addition, whenever, the analyser output is received by the microprocessor unit 18, the value obtained is checked for being within range. Whenever an error is detected it is displayed by the display 42 flashing E and the display 43 indicating the error number. Different errors are given numbers for ease of identification. The unit continues to function bypassing the specific sample point or specific channel having the error therein, unless the error occurs in the analyser or other common area to all sampling positions. To avoid sampling the defective channel, the distance switch 31 is set to zero. Recovery from an error is achieved by pressing the step button 44 after the channel has been bypassed or an error has been corrected.

In one embodiment the third level includes the LED which comes on when the third level is reached. If the level of contaminant gas at the next sampling from the same sampling position is at the same level or higher, then the LED flashes. If the contaminant gas level is lower, but still above the third level, the LED stays on, but does not flash. Timing systems may be included so that the unit is connected up to a clock by an interlock feature to operate only during the hours of work, and not at weekends, thus ensuring that maximum energy saving from heating or cooling is obtained. The interlock stops all non essential operation, but keeps equipment warm for instant restart. This feature reduces wear on the pump and analysis equipment, which in other systems is generally kept running continuously.

The contaminant gas defined in the embodiment is carbon dioxide gas present in the air. Other contaminent gas such as carbon monoxide which absorb certain frequencies may be monitored. Furthermore, humidity and temperature of the atmosphere at sampling points may also be measured and and the system can control humidifiers or dehumidifiers, and heaters, air conditioners, scrubbers, fans or fresh air vents.

Various changes may be made to the analyser without departing from the scope of the present invention, which is limited only by the following claims.

The embodiments of the invention in which an exclusive property or privilege is claimed are defined as follows:

1. Ambient air quality detection and control system for a plurality of sampling positions, comprising
    a sampling head located in each of the sampling positions,
    a pump for each sampling head, for pumping a sample of gas from each sampling head,
    a calibration pump having a filter means to provide clean gas,
    a selector means for selecting operation time of each pump individually and time lapse between sequences,
    an analyser for analysing samples of gas from each sampling head and the calibration pump, the analyser producing an analysis signal representing quantity of contaminant gas present in each sample,
    a flowline system with flow lines from each sampling head and the calibration pump, combining in a sample line to the analyser, the flow line system having no selector valves therein,
    means for setting a plurality of first predetermined set points representing levels of the contaminant gas which may occur in each sample,
    means for producing a plurality of on/off signals representing when the contaminant gas in each sample reaches the first set points,
    means for setting a second predetermined set point representing a level of the contaminant gas which may occur in each sample and a predetermined proportional range from the second set point for each sample, and
    means for producing an analog signal indicating a deviation from the second set point in the proportional range for each sample representing the contaminant gas in each sample, the analog signal for each sample being in a plurality of output ranges of different magnitudes.

2. The system according to claim 1 wherein the value of the analysis signal from each sample is indicated on a seven segment display in a sequence identifying the particular sampling head with the value for that sample, the sequence being on a preset time basis independent of which of the plurality of pumps is in operation.

3. The system according to claim 1 including a calibration means to operate with the calibration pump to produce a new zero base value and adjust the analysis signal accordingly, after a series of sequences and before commencing a further series of sequences.

4. The system according to claim 1 including a timing means associated with the selector means to set a predetermined time for the individual operation of each pump dependent upon the distance between the sampling head and the appropriate pump.

5. The system according to claim 1 including means for setting a time period for the commencement of a complete sequence to operate all the pumps in a desired order.

6. The system according to claim 1 including display means to indicate which pump is in operation.

7. The system according to claim 1 wherein in one of the output ranges, the analog signal for each sample is a pneumatic signal.

8. The system according to claim 1 wherein the analyser analyses the quantity of carbon dioxide gas present in the sample gas.

9. The system according to claim 8 wherein the analyser is an infrared analyser with a rotating chopper having a filter therein and the analysis signal represents the level of carbon dioxide gas present in each sample acquired at specific selected times synchronized with pump operating time representing distance from the sampling point to the analyser.

* * * * *